United States Patent [19]

Bruzzese

[11] 4,174,320

[45] Nov. 13, 1979

[54] PROCESS FOR THE PREPARATION OF RIFAMPICIN

[75] Inventor: Tiberio Bruzzese, Milan, Italy

[73] Assignee: Holco Investment Inc., Panama

[21] Appl. No.: 946,530

[22] Filed: Sep. 27, 1978

[30] Foreign Application Priority Data

Nov. 25, 1977 [GB] United Kingdom ............... 49148/77

[51] Int. Cl.$^2$ ........................................... C07D 498/18
[52] U.S. Cl. .......................... 260/239.3 P; 424/244; 424/248.54; 424/267
[58] Field of Search ................................... 260/239.3 P

[56] References Cited

U.S. PATENT DOCUMENTS

| | | | |
|---|---|---|---|
| 3,342,810 | 9/1967 | Maggi et al. | 260/239.3 P |
| 3,925,366 | 12/1975 | Marsili et al. | 260/239.3 P |
| 3,963,705 | 6/1976 | Marsili et al. | 260/239.3 P |

Primary Examiner—John M. Ford
Assistant Examiner—Robert T. Bond
Attorney, Agent, or Firm—Wenderoth, Lind & Ponack

[57] ABSTRACT

The present invention provides a process for the preparation of rifampicin, wherein rifamycin S is reacted in an aprotic dipolar solvent with a 1,3,5-trisubstituted hexahydro-1,3,5-triazine at a temperature from 20° to 100° C. followed by reaction with 1-amino-4-methylpiperazine, while keeping the pH in the range of from 5 to 7, whereafter the rifampicin formed is isolated.

15 Claims, No Drawings

4,174,320

PROCESS FOR THE PREPARATION OF RIFAMPICIN

BACKGROUND OF THE INVENTION

It is known that rifampicin is a compound with very good antibiotic properties which is used particularly as an antitubercular compound.

At present, only three processes for the manufacture of rifampicin are known, these being described in U.S. Pat. Nos. 3,342,810; 3,542,762 and 3,963,705.

According to U.S. Pat. No. 3,342,810, rifampicin is prepared by mildly oxidising a Mannich base of rifamycin SV and then mildly reducing the mixture thus obtained to give 3-formylrifamycin SV which is then reacted with 1-amino-4-methylpiperazine to form rifampicin.

According to U.S. Pat. No. 3,542,762, rifampicin is prepared by reacting rifamycin S with formaldehyde and with a primary aliphatic amine or with a condensation product thereof in the presence of manganese dioxide and then treating the reaction mixture with about 2 equivalents of 1-amino-4-methylpiperazine.

According to U.S. Pat. No. 3,963,705, rifampicin is obtained by reacting rifamycin S with an N-bis-alkoxymethyl-amine or an N-bis-hydroxymethyl-amine to give a well-defined intermediate compound, namely a 1,3-oxazino (5,6-c) rifamycin belonging to a well defined group of compounds specified in this Patent Specification which reacts in distinctly basic medium with the 1-amino-4-methylpiperazine to give rifampicin.

The process described in U.S. Pat. No. 3,342,810 has the disadvantage of requiring four successive reactions, beginning with the starting compound, rifamycin S, which have to be carried out with the isolation of two intermediate compounds, namely the Mannich base of rifamycin SV and of the 3-formylrifamycin SV. This means having to use several reaction vessels for the industrial production, involving high production costs and low yields.

This is also confirmed by the patentee of this U.S. Patent Specification who admits, in subsequent U.S. Pat. No. 3,542,762 that it is not economically advantageous, and defines the second process as being "much more convenient" (line 53, column 1).

The process of U.S. Pat. No. 3,542,762 has the disadvantage of requiring the reactions to be carried out in two different steps: condensation of rifamycin S to give a Mannich base and then oxidation to a Schiff base as the first step; then, after filtering off the manganese dioxide (this filtration is necessary because possible contact of even traces of manganese dioxide with 1-amino-4-methylpiperazine could give rise to explosion and fire), the second step is carried out involving two more reactions, namely, reduction of the Schiff base which is in the quinone form and then transimination of the hydroquinone Schiff base thus obtained to give rifampicin. This again involves high costs and low yields.

Both U.S. Pat. No. 3,342,810 and U.S. Pat. No. 3,542,762 involve oxidation reactions and successive reductions, with intermediate filtration, and, therefore, require the use of different reaction vessels.

According to U.S. Pat. No. 3,963,705, the reaction of rifamycin S with an N-bis-alkoxymethylamine or a N-bis-hydroxymethyl-amine necessarily gives rise to the formation, together with the 1,3-oxazino (5,6-c) rifamycin, of two molecules of alcohol or water which impair the reaction. This is demonstrated by the fact that the use of aprotic dipolar solvents is preferred; in fact, the same reaction carried out in the presence of the aprotic dipolar solvent (Example 14) gave a yield which was three times greater than that obtained with the use of n-propanol (Example 15).

According to the same U.S. Patent Specification, the intermediate compound 1,3-oxazino (5,6-c) rifamycin must be isolated in a solid state or by extraction with water-immiscible solvents and then reacted in a basic medium with 1-amino-4-methylpiperazine, meaning that the entire process is, in practice, carried out in two distinct steps.

As is known (J. Med. Chem., 11, 936/1968), the use of a basic medium can cause desacetylation and/or transacetylation of rifampicin, thus giving derivatives of rifampicin which do not have a useful antimicrobial activity: indeed, the transacetyl derivatives of rifampicin have practically no antibiotic activity in vitro, and the desacetyl derivative, although possessing antibiotic activity in vitro, is not absorbed (see Antibiotica et Chemotherapia, 16, 317/1970). Therefore, the use of basic media gives rise to impure rifampicin which requires purification by successive crystallisation, this decreasing the yield.

Finally, again referring to U.S. Pat. No. 3,963,705, independently of all the above considerations, repetition of the preparations described in the Examples, in spite of using identical experimental conditions, gave substantially lower yields than those reported.

It is an object of the present invention to provide a process for the preparation of rifampicin which can be carried out in one step and in one solvent system, without isolation of any intermediate compounds or phases.

Another object of the present invention is to provide a process by means of which it is possible to produce rifampicin with high yield and purity which, in particular, is substantially free of transacetylation and desacetylation derivatives of rifampicin.

SUMMARY OF THE INVENTION

Thus, according to the present invention, there is provided a process for the preparation of rifampicin, wherein rifamycin S is reacted with a 1,3,5-trisubstituted hexahydro-1,3,5-triazine in an aprotic dipolar solvent and optionally in the presence of formaldehyde, the reaction preferably being carried out without modifying the pH of the medium and preferably in the presence of certain acid substances, using controlled time and temperature conditions, whereafter 1-amino-4-methylpiperazine is then added directly to the reaction mixture, while keeping the pH value in the range of from 5 to 7, and then isolating the rifampicin formed.

DETAILED DESCRIPTION OF THE INVENTION

The 1,3,5-trisubstituted hexahydro-1,3,5-triazine used is preferably a 1,3,5-trialkyl-substituted or 1,3,5-triamine alkyl-substituted hexahydro-1,3,5-triazine. The alkyl substituents preferably contain up to 6 carbon atoms.

In the first stage of the new process, the reaction of rifamycin S with the 1,3,5-trisubstituted hexahydro-1,3,5-triazine and with formaldehyde, gives rise to the formation of 3-substituted 1,3-oxazino (5,6-c) rifamycins. These may be the same as those mentioned in U.S. Pat. No. 3,963,705 when, for example, the substituent is an alkyl radical or may be different from them when the substituent is an aminoalkyl radical; furthermore, in this phase of the reaction, the number of molecules of water formed is only half that formed by the method described in U.S. Pat. No. 3,963,705.

When, however, rifamycin S is reacted, without the use of formaldehyde, with an excess of 1,3,5-trisubstituted hexahydro-1,3,5-triazine, the reaction may proceed in the same way, if appropriate experimental conditions are adopted, to give corresponding 3-substituted 1,3-oxazino (5,6-c) rifamycins but, in this case, without the formation of water. This is surprising in view of the disclosures in U.S. Pat. No. 3,963,705, according to which the reaction of one molecule of an N-bis-hydroxymethyl-amine with one molecule of rifamycin S results in the formation of 2 molecules of water. It is also surprising that, contrary to this prior art, according to which, by reaction of a 1,3,5-trialkyl substituted hexahydro-1,3,5-triazine (constituted by the condensation product of formaldehyde with a primary alkyl amine in equimolecular amount) with an active hydrogen atom, such as that in the 3-position of rifamycin S, a Mannich base must necessarily be obtained, the above-mentioned process leads, instead, to the formation of a 3-alkyl-substituted 1,3-oxazino (5,6-c) rifamycin.

Another surprising and extremely important fact is that the 1-amino-4-methylpiperazine, which opens the 1,3-oxazino ring to give the final rifampicin, can be added directly to the reaction mixture, without isolating any intermediate product or phase and without changing the type of solvent, contrary to what is stated in U.S. Pat. No. 3,963,705.

Furthermore, the process can be carried out in an acid medium, thus avoiding the formation of desacetyl and/or transacetyl derivatives of rifampicin, again in contradistinction to what is stated in U.S. Pat. No. 3,963,705.

Reverting to a more detailed explanation of the whole procedure, we have found that, in the initial reaction with rifamycin S, it is possible to use several different hexahydro-1,3,5-triazines with various substituents in the 1,3,5-positions, particularly alkyl or aminoalkyl radicals. Furthermore, a possible process modification is the preparation of such triazines in situ simply by reacting equimolecular amounts of an alkylamine or aminoalkylamine with formaldehyde. Preferred alkyl radicals are those containing up to 6 carbon atoms, which can be straight or branched chained, typical radicals being methyl and tert.-butyl radicals, while the aminoalkyl radicals are particularly selected according to their basicity and structure to give best results and are generally tertiary amino radicals of the formula

with an open or preferably a cyclic structure, wherein R and R' represent alkyl radicals containing up to 3 carbon atoms or when taken together from said cyclic structure, typical radicals being 2-morpholinoethyl and 1-ethyl-3-piperidyl radicals.

In this first phase of the reaction, the 1,3-oxazino ring is closed by the use of formaldehyde, which can be employed as paraformaldehyde or as gaseous monomeric formaldehyde. In addition, we have, surprisingly, found that, by reacting rifamycin S with particular hexahydro-1,3,5-triazines and under particular experimental conditions, the addition of formaldehyde, whether polymeric or not, may be quite unnecessary, as such triazines themselves show the same action by readily liberating formaldehyde if present in appropriate excess. Generally speaking, 1,3,5-trialkyl-substituted hexahydro-1,3,5-triazines are able to react in this way, regardless of the pH of the reaction medium, whereas the 1,3,5-triaminoalkyl compounds can only do so in a more or less acidic medium.

The pH of the medium also plays an important role in a more general sense because the addition of medium strength acid substances, such as acetic acid or oxalic acid, not only enable the reaction speed to be increased but, what is more, limit the formation of certain by-products, particularly of rifamycin SV, which would otherwise be found unchanged at the end of the synthesis and, in some cases, could impair the purity and/or yield of the final rifampicin, an additional recrystallisation being required. The above discovery also constitutes an important feature of the present invention and, for the preparation of 3-aminoalkyl-substituted 1,3-oxazino (5,6-c) rifamycins, the addition of oxalic acid is particularly important for obtaining good results.

In the first phase of the reaction, the choice of solvent is very important. The solvent used is preferably a dipolar aprotic solvent, for example dimethylformamide, dimethylacetamide or dimethylsulphoxide: they are inert towards the reaction components involved, have a very high solvent power, which is necessary for carrying out the reaction in very concentrated phases and are able to increase the speed of the reaction. In addition, they are able selectively to direct the reaction in the desired sense, whereas when using an apolar, scarcely polar or protic solvent, the formation of undesired by-products may even predominate.

Under the conditions described and working at a temperature of from 20° to 100° C. and preferably of from 40° to 80° C., the first phase of reaction is generally concluded in 0.5 to 4 hours.

It is then obvious that, if it is desired to obtain the 1,3-oxazino (5,6-c) rifamycins as such, they can be obtained at this point by treating the reaction mixture with water at a moderately acid pH and then isolating them either by direct filtration or by extraction with appropriate solvents. In particular, the 3-aminoalkyl-1,3-oxazino (5,6-c) rifamycins, which are new compounds, possess a high antibiotic activity against numerous bacterial strains and are more powerful than analogous 3-alkyl-substituted derivatives.

If, on the other hand, the required product is rifampicin, the reaction is continued in the second phase of the process in which the 3-alkyl- or the 3-aminoalkyl-1,3-oxazino (5,6-c) rifamycin is reacted with 1-amino-4-methylpiperazine to give rifampicin; one of the characterising features of the new process is that the intermediate oxazino derivative does not need to be isolated and it is also not necessary to replace the aprotic dipolar solvent initially used with a second "inert organic solvent which is immiscible with water", as is the case in U.S. Pat. No. 3,963,705. On the contrary, the 1-amino-4-methylpiperazine can be added directly to the crude intermediate in its preparation medium and the solvent does not have to be replaced. In this respect, the use of the same aprotic dipolar solvent already used in the first phase of preparation, besides improving the process both technologically and economically, also helps to increase the reaction speed.

In quite a surprising way, it was then observed that the reaction proceeds better, if not with regard to speed, certainly as far as purity is concerned (the formation of desacetylation and/or transacetylation products of rifampicin thus being avoided), when the pH of the medium is moderately acidic. Therefore, if the first phase of the reaction is carried out in acid solution, which is preferred, the reaction with 1-amino-4-methylpiperazine is continued as such unless additional quantities of acid are needed to bring the pH to 5–7; otherwise the entire quantity of acid must be added at this point. In any case, the addition of basic substances in order to produce alkaline reaction conditions is avoided.

As previously mentioned, numerous organic acids may be used, especially acetic acid; in particular cases, the best results are achieved with oxalic acid and, in any case, a pH value of from 5 to 7 gives optimum results. Under these experimental conditions and at a temperature of from 20° to 80° C. and preferably of from 40° to 50° C., the reaction giving rifampicin is completed easily and rapidly within a period of 20 to 60 minutes. The product is then isolated by the usual procedures, for example, by treating the reaction mixture with water under weakly acidic conditions and then extracting with an appropriate organic solvent which is immiscible with water and thoroughly washing the organic extract. After drying, the desired product is obtained, by evaporating to dryness, in high or even quantitative yields and with a high degree of purity.

Some of the following Examples, such as Example 5, describe for the whole process from rifamycin S an almost quantitative yield of sufficiently pure rifampicin and, after optional recrystallisation, the yield is more than 90% of the theoretical value. This yield is much higher than the actual yields obtained by repetition of the previously known processes.

The following Examples are given for the purpose of illustrating the present invention:

EXAMPLE 1

15 g. Rifamycin S are dissolved in 50 ml. anhydrous dimethylformamide at ambient temperature and 3.66 g. of 1,3,5-tri-(tert.-butyl)-hexahydro-1,3,5-triazine and 1.29 g. paraformaldehyde are then added to the solution. The reaction mixture is kept at 75° C. for about 3 hours until the reaction is complete, with the formation of 3-tert.-butyl-1,3-oxazino (5,6-c) rifamycin (thin layer chromatography on silica gel 60 F$_{254}$ (Merck): blue spot at Rf 0.73; eluent chloroform:methanol 9:1 v/v). The reaction mixture is then cooled to 50° C. and a solution (acidified to pH 5.5–6 with acetic acid) prepared from 8.65 g. 1-amino-4-methylpiperazine in 15 ml. dimethylformamide is added. After stirring for about 1 hour at 50° C. until the blue spot in thin layer chromatogram disappears, water acidified with 2% acetic acid is added to the resulting solution, followed by extraction with 400 ml. chloroform in portions and repeatedly washing the chloroform extract with water. After drying with anhydrous sodium sulphate and filtering, the solvent is evaporated to dryness. The residue (16 g.) is crystallised from acetone to give 10.6 g. of chromatographically pure rifampicin.

EXAMPLE 2

15 g. Rifamycin S are dissolved in 50 ml. dimethylformamide and 5.5 g. 1,3,5-tri-(tert.-butyl)-hexahydro-1,3,5-triazine are added to the solution. The reaction mixture is then kept at 75° C. for about 3 hours and 1-amino-4-methylpiperazine, acidified with acetic acid, added directly according to the procedure described in Example 1, followed by analogous working up to give substantially pure rifampicin.

EXAMPLE 3

2.8 g. Rifamycin S are dissolved in 10 ml. anhydrous dimethyl sulphoxide and then 0.68 g. 1,3,5-tri-(tert.-butyl)-hexahydro-1,3,5-triazine and 0.24 g. paraformaldehyde are added thereto. The reaction mixture is kept at 75° C. for about 3 hours until the reaction of the rifamycin S is complete and then cooled to 50° C., whereafter 1.6 g. 1-amino-4-methylpiperazine, diluted with 5 ml. dimethyl sulphoxide and acidified to pH 6 with acetic acid, are added directly thereto. Continuing the reaction as described in Example 1, the desired rifampicin is then obtained.

EXAMPLE 4

1.29 g. Paraformaldehyde and 3.66 g. 1,3,5-tri-(tert.-butyl)-hexahydro-1,3,5-triazine are added, with stirring, to a solution of 15 g. rifamycin S in a mixture of 50 ml. dimethylformamide and 5 g. acetic acid. The reaction mixture is kept at 75° C. for about 1 hour, whereafter the reaction is complete, then cooled to 50° C. and 6.68 g. 1-amino-4-methylpiperazine added thereto, with stirring. The solution is kept at 50° C. for about 1 hour and, when the reaction is completed, diluted with 10 volumes of a 2% aqueous solution of acetic acid and extracted with chloroform. The organic extract is then washed thoroughly with water, dried over anhydrous sodium sulphate and the solvent evaporated to dryness, to give 17.2 g. of a residue of the desired rifampicin. The product obtained is crystallised from acetone-ethyl acetate to give 13.3 g. pure rifampicin.

EXAMPLE 5

To a solution of 70 g. rifamycin S in 250 ml. dimethylformamide are successively added, with stirring, 24 g. acetic acid, 6 g. paraformaldehyde and 17 g. 1,3,5-tri-(tert.-butyl)-hexahydro-1,3,5-triazine as described in Example 4. The mixture is stirred at 50° C. for about 1 hour and then, at the same temperature, 31 g. 1-amino-4-methylpiperazine are added. After reaction for another hour at 50° C., the reaction product is isolated as described in Example 4, to give 81 g. of product of good purity which, after crystallisation, if needed, gives 74.5 g. pure rifampicin.

EXAMPLE 6

2.9 g. tert.-Butylamine and 1.2 g. paraformaldehyde and then 14 g. rifamycin S, 4.8 g. of acetic acid and 1.2 g. paraformaldehyde are added successively to 50 ml. dimethyl formamide, while stirring. After reaction for 3 hours at 50° C., 6.2 g. 1-amino-4-methylpiperazine are added and the reaction is continued as described in Example 4 to give, as above, pure rifampicin.

EXAMPLE 7

To a solution of 2.8 g. rifamycin S in 10 ml. dimethylformamide is added 0.36 g. oxalic acid and then 0.24 g. paraformaldehyde and 0.68 g. 1,3,5-tri-(tert.-butyl)-hexahydro-1,3,5-triazine. The reaction mixture is kept at 75° C. for about 1 hour until the reaction is complete, then cooled to 50° C. and 1.7 g. 1-amino-4-methylpiperazine, diluted with 3 ml. dimethylformamide and acidified to pH 6 with acetic acid, are added thereto. The reaction is continued at 50° C. for about 1 hour until completed, then diluted with water acidified to 2% with acetic acid and the mixture extracted with chloroform. Following the above described process, the desired rifampicin is obtained in high yield.

EXAMPLE 8

0.36 g. Oxalic acid and 1.0 g. 1,3,5-tri-(tert.-butyl)-hexahydro-1,3,5-triazine are added to a solution of 2.8 g. rifamycin S in 10 ml. dimethylformamide. The mixture is kept at 75° C. for about 1 hour, then 1.7 g. of acidified 1-amino-4-methylpiperazine are added directly, according to the process described in Example 7. The chloroform extract finally obtained is concentrated to a small volume and diluted with an appropriate mixture of ethyl acetate-acetone to give a high yield of pure rifampicin.

EXAMPLE 9

7 g. Rifamycin S are dissolved in 25 ml. dimethylformamide, then, while stirring, there are successively added 2.4 g. acetic acid, 0.6 g. paraformaldehyde and 0.85 g. 1,3,5-trimethyl-hexahydro-1,3,5-triazine. The mixture is then kept at 50° C. for 3 hours until the reaction is completed, with the formation of 3-methyl-1,3-oxazino (5,6-c) rifamycin (thin layer chromatography on silica gel 60 $F_{254}$ - Merck: blue spot at Rf 0.19, eluent chloroform:methanol 9:1 v/v). 3.1 g. 1-amino-4-methylpiperazine are then added and the reaction is continued at 50° C. for about 1 hour until it is completed, as demonstrated by the disappearance of the blue spot in the TLC. After treatment in the usual way, a high yield (7.2 g.) of rifampicin is obtained. It can easily be purified by crystallisation from acetone.

EXAMPLE 10

0.72 g. Oxalic acid, 0.48 g. paraformaldehyde and 2.28 g. 1,3,5-tri-(2-morpholinoethyl)-hexahydro-1,3,5-triazine are added to a solution of 5.6 g. rifamycin S in 20 ml. dimethylformamide. The mixture is brought to 75° C. and kept at this temperature for about 1 hour until the reaction is complete, as shown by the disappearance of the rifamycin S (TLC) and the formation of 3-(2-morpholinoethyl)-1,3-oxazino (5,6-c) rifamycin (thin layer chromatography on silica gel 60 $F_{254}$ (Merck): blue spot at Rf 0.37, eluent chloroform:methanol 9:1 v/v). The reaction mixture is cooled to 50° C. and a solution of 3.4 g. 1-amino-4-methylpiperazine in 5 ml. dimethylformamide, appropriately acidified to pH 6 with acetic acid, is added directly thereto. It is then heated, while stirring, for about another hour until the reaction is completed, as shown by the disappearance of the blue spot in the TLC. Then, after dilution with 2% aqueous acetic acid and extraction of the resulting suspension with chloroform, the organic solution is washed thoroughly with water and evaporated to dryness. The residue (5.5 g.) is then crystallised from acetone-ethyl acetate to give 4 g. pure rifampicin.

EXAMPLE 11

2.8 g. Rifamycin S are dissolved in 10 ml. dimethylformamide, then 0.24 g. paraformaldehyde and 1.4 g. 1,3,5-tri-(2-morpholinoethyl)-hexahydro-1,3,5-triazine oxalate are added thereto. The reaction mixture is heated at 75° C. until the reaction is completed (about 4 hours), then cooled to 50° C. and 1-amino-4-methyl-piperazine, appropriately acidified with acetic acid, is added directly, according to the process described in Example 10, to give, as above, the desired rifampicin.

EXAMPLE 12

14 g. Rifamycin S are dissolved in 50 ml. dimethylformamide at 20° C., then 1.8 g. oxalic acid and 5.5 g. 1,3,5-(2-morpholinoethyl)-hexahydro-1,3,5-triazine are added to the solution and a stream of monomeric formaldehyde and dry nitrogen is bubbled in for 20 minutes, whereafter the reaction mixture is heated at 70° C. to complete the reaction. A solution of 8.5 g. 1-amino-4-methylpiperazine in 10 ml. dimethylformamide, acidified to pH 5 with acetic acid, is added to the resulting solution, which is then stirred at 40° C. until the disappearance of the blue spot in the thin layer chromatogram. 150 ml. dichloromethane are added to the resulting solution and the mixture is washed several times with water and dried over anhydrous sodium sulphate. After filtration, the solvent is evaporated to dryness and the residue is crystallised from acetone to give 10.7 g. of chromatographically pure rifampicin.

EXAMPLE 13

0.72 g. Oxalic acid and 3.4 g. 1,3,5-tri-(2-morpholinoethyl)-hexahydro-1,3,5-triazine are added to a solution of 5.6 g. rifamycin S in 20 ml. dimethylformamide. The reaction mixture is then heated at 75° C. for about 3 hours and 1-amino-4-methylpiperazine, in an acid medium is added analogously to the process described in Example 10. Subsequently, the chloroform solution is distilled to give the desired rifampicin (5.8 g.) which can readily be crystallised from acetone.

EXAMPLE 14

Rifamycin S is reacted with 1,3,5-tri-(2-morpholinoethyl)-hexahydro-1,3,5-triazine and with paraformaldehyde in the presence of oxalic acid, following essentially the process described in Example 10 but using dimethylacetamide as solvent. After the addition of 1-amino-4-methylpiperazine and proceeding as previously described, substantially pure rifampicin is isolated in similar yield.

EXAMPLE 15

A solution of 2.8 g. rifamycin S in 10 ml. dimethylformamide is treated with 0.36 g. oxalic acid, 0.24 g. paraformaldehyde and 1.12 g. 1,3,5-tri-(1-ethyl-3-piperidyl)-hexahydro-1,3,5-triazine. The reaction mixture is then heated to 75° C. for about 1 hour, until the reaction is complete, to give 3-(1-ethyl-3-piperidyl)-1,3-oxazino (5,6-c) rifamycin (thin layer chromatography on silica gel 60 $F_{254}$ (Merck): blue spot at Rf 0.40, eluent chloroform:methanol 9:1 v/v). After cooling to 50° C., 1.7 g. 1-amino-4-methylpiperazine, acidified to pH 6 with acetic acid, are added and the reaction is continued according to Example 10 to give 3.1 g. of crude rifampicin which is crystallised from an appropriate solvent to give a high yield (2.5 g.) of pure product.

EXAMPLE 16

0.9 g. Oxalic acid, 0.6 g. paraformaldehyde and 2.85 g. 1,3,5-tri-(2-morpholinoethyl)-hexahydro-1,3,5-triazine are added to a solution of 7 g. rifamycin S in 25 ml. dimethylformamide. The reaction mixture is then heated to 75° C. for 1 hour until the rifamycin S has completely reacted (TLC). 10 volumes of a 2% solution of acetic acid in water are added and the suspension obtained is extracted with chloroform and the extract repeatedly washed with water. After drying over anhydrous sodium sulphate and distilling off the solvent, a residue is obtained comprising 7.5 g. 3-(2-morpholinoethyl)-1,3-oxazino (5,6-c) rifamycin which is then purified (small quantities of rifamycin SV are formed during the preparation) with appropriate solvent mixtures.

Alternatively, the product is isolated, after dilution of the reaction mixture with acidic water, by directly filtering the suspension obtained and thoroughly washing and then vacuum drying the collected material. Purification can also be carried out with standard techniques, such as column chromatography on silica gel (0.05–0.2 mm., Merck), eluting first with chloroform only to remove possible impurities and then with appropriate solvent mixtures with a maximum 5% by volume of methanol in order to recover the pure product after distilling off the solvents.

3-(2-Morpholinoethyl)-1,3-oxazino (5,6-c) rifamycin is obtained in the form of blue crystals with an Rf value of 0.37 on a thin layer chromatogram (silica gel 60 F$_{254}$ Merck; eluent, chloroform:methanol 9:1 v/v), and a characteristic IR spectrum with absorption peaks (Nujol mull) at 3440, 1720-1708, 1650, 1606, 1550, 1520, 1258, 1230, 1160, 1118, 1063, 970 and 900 cm$^{-1}$.

The substance has a high antibiotic activity against several bacterial strains and is more potent than similar 3-alkyl-substituted 1,3-oxazine (5,6-c) rifamycins, showing, for example, the following minimum inhibitory concentration values (in brackets, for comparison, values obtained with the 3-tert.-butyl derivative): *Staphylococcus aureus*, 0.031 mcg/ml. (0.125); *Streptococcus faecalis*, 0.25 mcg/mg. (0.5); and *Bacillus subtilis*, 1.0 mcg/ml. (2.0).

I claim:

1. A process for the preparation of rifampicin, wherein rifamycin S is reacted in an aprotic dipolar solvent with a 1,3,5-trisubstituted hexahydro-1,3,5-triazine at a temperature from 20° to 100° C. followed by reaction with 1-amino-4-methylpiperazine, while keeping the pH in the range of from 5 to 7, whereafter the rifampicin formed is isolated.

2. A process according to claim 1, wherein the reaction of rifamycin S with 1,3,5-trisubstituted hexahydro-1,3,5-triazine is carried out in the presence of formaldehyde.

3. A process according to claim 2, wherein the formaldehyde is used in polymeric form.

4. A process according to claim 2, wherein the formaldehyde is used in monomeric gaseous form.

5. A process according to claim 1, wherein the reaction of rifamycin S with 1,3,5-trisubstituted hexahydro-1,3,5-triazine is carried out in the presence of an organic acid.

6. A process according to claim 5, wherein the organic acid is acetic acid or oxalic acid.

7. A process according to claim 1, wherein said 1,3,5-trisubstituted hexahydro-1,3,5-triazine is one in which the substituents are lower aliphatic radicals or radicals of the formula

wherein R and R' each represent open chain alkyl radicals or R and R' taken together form a cyclic structure including N.

8. A process according to claim 7, wherein the lower aliphatic radicals are methyl or tert.-butyl radicals.

9. A process according to claim 7, wherein the radicals having a cyclic structure are 2-morpholinoethyl or 1-ethyl-3-piperidyl radicals.

10. A process according to claim 1, wherein the aprotic dipolar solvent is dimethylformamide, dimethyl acetamide or dimethyl sulphoxide.

11. A process according to claim 1, wherein the 1-amino-4-methylpiperazine is dissolved in an aprotic dipolar solvent before being added to said reaction mixture.

12. A process according to claim 11, wherein the solution of 1-amino-4-methylpiperazine is acidified to a pH of from 5 to 7 by the addition of acetic acid or oxalic acid.

13. 3-Aminoalkyl-1,3-oxazino (5,6-c) rifamycin.

14. 3-(2-Morpholinoethyl)-1,3-oxazino (5,6-c) rifamycin.

15. 3-(1-Ethyl-3-piperidyl)-1,3-oxazino (5,6-c) rifamycin.

* * * * *